US008318474B1

(12) United States Patent
Smolke et al.

(10) Patent No.: US 8,318,474 B1
(45) Date of Patent: Nov. 27, 2012

(54) ENGINEERED YEAST CELLS AND USES THEREOF

(75) Inventors: Christina D. Smolke, Pasadena, CA (US); Kristy Hawkins, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1486 days.

(21) Appl. No.: 11/439,876

(22) Filed: May 23, 2006

Related U.S. Application Data

(60) Provisional application No. 60/683,824, filed on May 23, 2005.

(51) Int. Cl.
C12N 1/00 (2006.01)
C12N 1/19 (2006.01)
C12N 15/63 (2006.01)
C12P 21/00 (2006.01)

(52) U.S. Cl. .............. 435/255.1; 435/254.2; 435/320.1; 435/71.1

(58) Field of Classification Search .................. None
See application file for complete search history.

(56) References Cited

OTHER PUBLICATIONS

Donini et al. Allelism of IMP1 and GAL2 genes of *Saccharomyces cerevisiae*. J Bacteriol. May 1992;174(10):3411-5.*
Lohr et al. Transcriptional regulation in the yeast GAL gene family: a complex genetic network. FASEB J. Jun. 1995;9(9):777-87.*
Acar et al., "Enhancement of cellular memory by reducing stochastic transitions," *Nature* 435:228-232 (2005).
Alton et al., "Nucleotide sequence analysis of the chloramphenicol resistance transposon Tn9," *Nature* 282:864-869 (1979).
Baldwin et al., "Cloning of the luciferase structural genes from *Vibrio harveyi* and expression of bioluminescence in *Escherichia coli*," *Biochemistry* 23:3663-3667 (1984).
Belli et al., "An activator/repressor dual system allows tight tetracycline-regulated gene expression in budding yeast," *Nucleic Acids Res* 26:942-947 (1998).
Benoist et al., "In vivo sequence requirements of the SV40 early promoter region," *Nature* 290:304-310 (1981).
Bhat et al., "Analysis of the GAL3 signal transduction pathway activating GAL4 protein-dependent transcription in *Saccharomyces cerevisiae*," *Genetics* 125:281-291 (1990).
Bhat et al., "Stochastic variation in the concentration of a repressor activates GAL genetic switch: implications in evolution of regulatory network," *FEBS Lett* 579:597-603 (2005).
Cullen et al., "Secreted placental alkaline phosphatase as a eukaryotic reporter gene," *Methods Enzymol* 216:362-368 (1992).
de Wet et al., "Firefly luciferase gene: structure and expression in mammalian cells," *Mol Cell Biol* 7:725-737 (1987).
Engebrecht et al., "Identification of genes and gene products necessary for bacterial bioluminescence," *Proc Natl Acad Sci USA* 81:4154-4158 (1984).
Foecking et al., "Powerful and versatile enhancer-promoter unit for mammalian expression vectors," *Gene* 45:101-105 (1986).

Funk et al., "Vector systems for heterologous expression of proteins in *Saccharomyces cerevisiae*," *Methods Enzymol* 350:248-257 (2002).
Gari et al., "A set of vectors with a tetracycline-regulatable promoter system for modulated gene expression in *Saccharomyces cerevisiae*," *Yeast* 13:837-848 (1997).
Gietz et al., "Transformation of yeast by lithium acetate/single-stranded carrier DNA/polyethylene glycol method," *Methods Enzymol* 350:87-96 (2002).
Glick et al., "Factors affecting the expression of foreign proteins in *Escherichia coli*," *J Ind Microbiol* 1:277-282 (1987).
Hall et al., "Expression and regulation of *Escherichia coli* lacZ gene fusions in mammalian cells," *J Mol Appl Genet* 2:101-109 (1983).
Hamer et al., "Regulation in vivo of a cloned mammalian gene: cadmium induces the transcription of a mouse metallothionein gene in SV40 vectors," *J Mol Appl Genet* 1:273-288 (1982).
Hawkins et al., "The regulatory roles of the galactose permease and kinase in the induction response of the GAL network in *Saccharomyces cerevisiae*," *J Biol Chem* 281:13485-13492. (2006).
Horak et al., "Catabolite inactivation of the galactose transporter in the yeast *Saccharomyces cerevisiae*: ubiquitination, endocytosis, and degradation in the vacuole," *J Bacteriol* 179:1541-1549 (1997).
Johnston et al., "Isolation of the yeast regulatory gene GAL4 and analysis of its dosage effects on the galactose/melibiose regulon," *Proc Natl Acad Sci USA* 79:6971-6975 (1982).
Khlebnikov et al., "Homogeneous expression of the $P_{(BAD)}$ promoter in *Escherichia coli* by constitutive expression of the low-affinity high-capacity AraE transporter," *Microbiology* 147:3241-3247 (2001).
Koller et al., "The CUP1 promoter of *Saccharomyces cerevisiae* is inducible by copper in *Pichia pastoris*," *Yeast* 16:651-656 (2000).
Koshland, "The era of pathway quantification," *Science* 280:852-853 (1998).
Lamphier et al., "Multiple mechanisms mediate glucose repression of the yeast GAL1 gene," *Proc Natl Acad Sci USA* 1:5922-5926 (1992).
Li et al., "Green fluorescent protein in *Saccharomyces cerevisiae*: real-time studies of the GAL1 promoter," *Biotechnol Bioeng* 70:187-196 (2000).
Longtine et al., "Additional modules for versatile and economical PCR-based gene deletion and modification in *Saccharomyces cerevisiae*," *Yeast* 14:953-961 (1998).
Louis et al., "Binary and graded responses in gene networks," *Sci STKE* 2002(143):PE33 (2002).
Mascorro-Gallardo et al., "Construction of a CUP1 promoter-based vector to modulate gene expression in *Saccharomyces cerevisiae*," *Gene* 172:169-170 (1996).

(Continued)

*Primary Examiner* — Michele K Joike
(74) *Attorney, Agent, or Firm* — McCarter & English, LLP; Elizabeth A. Hanley, Esq.; Yu Lu

(57) ABSTRACT

The present application provides engineered yeast cells and uses thereof. In specific embodiments, the yeast cells have a mutation in the GAL2 gene. In specific embodiments, the yeast cells can be used for producing a protein or compound of interest.

24 Claims, 11 Drawing Sheets

OTHER PUBLICATIONS

Mateus et al., "Destabilized green fluorescent protein for monitoring dynamic changes in yeast gene expression with flow cytometry," *Yeast* 16:1313-1323 (2000).

McKnight, "Functional relationships between transcriptional control signals of the thymidine kinase gene of herpes simplex virus," *Cell* 31:355-365 (1982).

Morgan-Kiss et al., "Long-term and homogeneous regulation of the *Escherichia coli* araBAD promoter by use of a lactose transporter of relaxed specificity," *Proc Natl Acad Sci USA* 28:7373-7377 (2002).

Nehlin et al., "Control of yeast GAL genes by MIG1 repressor: a transcriptional cascade in the glucose response," *EMBO J* 10:3373-3377 (1991).

Peng et al., "Gene activation by interaction of an inhibitor with a cytoplasmic signaling protein," *Proc Natl Acad Sci USA* 99:8548-8553 (2002).

Ramos et al., "Characteristics of galactose transport in *Saccharomyces cerevisiae* cells and reconstituted lipid vesicles," *J Bacteriol* 171:3539-3544 (1989).

Rhodes et al., "A yeast-*Escherichia coli* shuttle vector containing the M13 origin of replication," *Plasmid* 23:159-162 (1990).

Ruhela et al., "Autoregulation of regulatory proteins is key for dynamic operation of GAL switch in *Saccharomyces cerevisiae*," *FEBS Lett* 576:119-126 (2004).

Schell et al., "Purification and properties of galactokinase from *Saccharomyces cerevisiae*," *J Biol Chem* 252:1162-1166 (1977).

Schleif et al., "Regulation of the L-arabinose Catabolic Operon araBAD," in *Transcriptional Regulation*. 643-665, Cold Spring Harbor Press, Cold Spring Harbor (1992).

Sikorski et al., "A system of shuttle vectors and yeast host strains designed for efficient manipulation of DNA in *Saccharomyces cerevisiae*," *Genetics* 122:19-27 (1989).

Silver et al., "Amino terminus of the yeast GAL4 gene product is sufficient for nuclear localization," *Proc Natl Acad Sci USA* 81:5951-5955 (1984).

Solow et al., "Heterologous protein production from the inducible MET25 promoter in *Saccharomyces cerevisiae*," *Biotechnol Prog* 21:617-620 (2005).

Stagoj et al., "Fluorescence based assay of GAL system in yeast *Saccharomyces cerevisiae*," *FEMS Microbiol Lett* 244:105-110 (2005).

Thoden et al., "Molecular structure of *Saccharomyces cerevisiae* Gal1p, a bifunctional galactokinase and transcriptional inducer," *J Biol Chem* 280:36905-36911 (2005).

Toh et al., "Isolation and characterization of a rat liver alkaline phosphatase gene. A single gene with two promoters," *Eur J Biochem* 182:231-237 (1989).

Verma et al., "Quantitative analysis of GAL genetic switch of *Saccharomyces cerevisiae* reveals that nucleocytoplasmic shuttling of Gal80p results in a highly sensitive response to galactose," *J Biol Chem* 278:48764-48769 (2003).

Verma et al., "Expression of GAL genes in a mutant strain of *Saccharomyces cerevisiae* lacking GAL80: quantitative model and experimental verification," *Biotechnol Appl Biochem* 39(Pt 1): 89-97 (2004).

Wolfe et al., "Molecular evidence for an ancient duplication of the entire yeast genome," *Nature* 387:708-713 (1997).

Yen et al., "An improved tetO promoter replacement system for regulating the expression of yeast genes," *Yeast* 20:1255-1262 (2003).

Batista, A.S., et al., "Sucrose Fermentation by *Saccharomyces cerevisiae* Lacking Hexose Transport," J. Mol. Microbiol. Biotechnol., 8:26-33 (2004).

Donnini, C., et al., "Allelism of IMP1 and GAL2 Genes of *Saccharomyces cerevisiae*," *J. Bacteriology*, 174(10):3411-3415 (1992).

Tschopp, J.F., et al., "GAL2 Codes for a Membrane-Bound Subunit of the Galactose Permease in *Saccharomyces cerevisiae*," J. Bacteriology, 166(1):313-318 (1986).

Wieczorke, R., et al., "Concurrent knock-out of at least 20 transporter genes is required to block uptake of hexoses in *Saccharomyces cerevisiae*," *FEBS Letters*, 464:123-128 (1999).

* cited by examiner

Figure 7

| Strain Number | Genotype | Plasmid |
|---|---|---|
| W303α | MATα his3-11,15 trp1-1 leu2-3 ura3-1 ade2-1 | |
| CSY22 | gal2D | |
| CSY13 | Gal2p::KanMX6-tTA-tetO₂ | |
| CSY50 | wild-type | pGAL-GFP |
| CSY52 | gal2D | pGAL-GFP |
| CSY40 | Gal2p::KanMX6-tTA-tetO₂ | pGAL-GFP |
| CSY53 | gal1D | pGAL-GFP |
| CSY54 | gal1D gal2D | pGAL-GFP |
| CSY55 | gal1D Gal2p::KanMX6-tTA-tetO₂ | pGAL-GFP |
| CSY89 | Gal3p::KanMX6-tTA-tetO2 | pGAL-GFP |
| CSY90 | Gal80p::His3MX6-tTA-tetO₂ | pGAL-GFP |
| CSY91 | Gal3p::KanMX6-tTA-tetO₂ Gal80p::His3MX6-tTA-tetO₂ | pGAL-GFP |

* All strains are derivatives of W303α; only modifications to the wild-type background are indicated.

ENGINEERED YEAST CELLS AND USES THEREOF

CROSS-REFERENCE TO RELATED APPLICATIONS

This application claims priority to and the benefit of U.S. Provisional Application No. 60/683,824, filed on May 23, 2005, the content of which is hereby incorporated by reference in its entirety.

BACKGROUND OF THE INVENTION

Conventional means for obtaining organic or protein molecules are often insufficient. Organic compounds are often extracted from biological materials (e.g., plants, microbes, and animals) or synthesized in the laboratory. Organic synthesis is usually complex since several steps are required to obtain the desired product. Furthermore, these steps often involve the use of toxic solvents, which require special handling and disposal. Extraction of organic compounds from biological materials may also require toxic solvents. In addition, extraction and purification methods usually provide a low yield of the desired compound, as biological materials typically contain only small quantities of these compounds.

Inducible promoter systems have been used to increase in vivo production of organic or protein molecules. Many of these systems, however, lack the ability to regulate the expression of the desired compound. For example, *Saccharomyces cerevisiae* inducible promoter systems have long been used for expression of heterologous proteins. Native inducible promoters such as GAL1 (Funk et al. (2002) *Methods Enzymol.* 350, 248-257), MET25 (Solow et al. (2005) *Biotechnol. Prog.* 21, 617-620), and CUP1 (Koller et al. (2000) *Yeast* 16, 651-656 and Mascorro-Gallardo et al. (1996) *Gene* 172, 169-170), although used successfully without modification, exhibit certain properties that are undesirable for the production of proteins and organic compounds. One common feature of these systems is their autocatalytic or switch-like behavior, where addition of small amounts of inducer leads to large increases in gene expression. In prokaryotes and bacteriophages, this is generally due to cooperative interactions between transcription factors and promoter elements. In more complex eukaryotic networks, other elements such as feedback loops, zero-order sensitivity, multi-step signaling mechanisms, and nucleocytoplasmic transport of regulatory proteins (Koshland (1998) *Science* 280, 852-853 and Verma et al. (2003) *J. Biol. Chem.* 278, 48764-48769) often contribute to nonlinear responses. In addition, native inducible promoter systems are often characterized by an all-or-none effect, in which genes are either maximally expressed or virtually not expressed in individual cells (Louis et al. (2002) *Sci. STKE* 2002, PE33). The inability to regulate gene expression in these inducible promoter systems can present problems such as toxicity, due to overproduction of the expressed compound. The inability to readily produce large quantities of many biological compounds has limited their practical use in areas such as drug production. Accordingly, there is a need for in vivo expression systems that can be tuned and regulated.

SUMMARY OF THE INVENTION

The present invention relates to engineered microorganisms comprising gene networks that allow for the regulation of production of a protein or compound of interest. This invention also relates to methods for regulating the production of a protein or compound of interest in cells, such as for example yeast cells.

In certain aspects, the invention provides methods and compositions for controlling production of a compound of interest in cells, such as for example yeast cells.

A first aspect of the invention provides a method for regulating the production of a protein of interest in yeast. The method includes providing a yeast cell with a mutation in the GAL2 gene, and the yeast cell further comprises a nucleic acid encoding a protein of interest that is operably linked to a GAL-responsive promoter. The method further includes contacting the cell with a molecule, such as for example a galactose or an analog thereof, which the GAL-responsive promoter responds to and alters the expression of the nucleic acid. In specific embodiments, the GAL-responsive promoter has a linear or substantially linear response to the molecule, such that contacting the cell with a greater amount of the molecule leads to a greater alteration of expression of the nucleic acid, thereby regulating the production of the protein of interest. In specific embodiments, the linear or substantially linear response is tunable. In certain embodiments, contacting the cell with a greater amount of the molecule leads to an increase of expression of the nucleic acid, thereby increasing the production of the protein of interest. In certain embodiments, contacting the cell with a greater amount of the molecule leads to an decrease of expression of the nucleic acid, thereby decreasing the production of the protein of interest; in certain embodiments, the yeast cell further comprises a mutation in one or more of the following genes: GAL1, GAL4, GAL80, and GAL3. In certain embodiments, the mutation in GAL4, GAL80, or GAL3 alters a biological activity of the corresponding protein (GAL4, GAL80, or GAL3, respectively). In certain embodiments, the protein of interest regulates the production of a compound of interest, and the method thereby can be employed for producing a compound of interest. In specific embodiments, the protein of interest regulates the production of the compound of interest through a metabolic pathway, which can be an endogenous pathway or a genetically engineered pathway.

Accordingly, the invention provides a method for regulating the production of a protein of interest in yeast. In certain embodiments, the method includes providing a yeast cell with a mutation in the GAL2 gene; the yeast cell contains a nucleic acid encoding a protein operably linked to a GAL-responsive promoter, and the protein regulates the production of a compound of interest. The method further comprises contacting the cell with a molecule that the promoter responds to, such as for example a galactose or an analog thereof, and increases the expression of the protein from the nucleic acid (that is, the promoter is an inducible or activatable promoter with respect to the molecule). Thus, contacting the cell with a greater amount of the molecule leads to a greater amount of expression of the protein from the nucleic acid, thereby regulating the production of the compound of interest.

The invention further provides a method for regulating the production of a compound of interest in yeast, including: providing a cell with a mutation in one or more of the following genes, GAL1, GAL2, GAL4, GAL80, and GAL3; the yeast cell contains a nucleic acid encoding a protein operably linked to a GAL-responsive promoter, and the protein regulates the production of a compound of interest. The method further includes contacting the cell with a molecule that the promoter responds to and decreases the expression of the nucleic acid. Accordingly, the promoter is a repressible promoter with respect to the molecule. Thus, contacting the cell with a greater amount of the molecule leads to a lower amount of expression of the nucleic acid, thereby regulating the production of the compound of interest.

Certain methods and compositions employ a yeast cell comprising a mutation in the GAL2 gene. In specific embodiments, the mutation in the GAL2 gene leads to or results in decreased amount of GAL2 available to or the removal of GAL2 from the GAL network in the yeast cell. In certain embodiments, the GAL2 gene is operably linked to an inducible promoter, a constitutive promoter, or a repressible promoter, such as for example, a CUP promoter, a MET promoter, a PHO promoter, and a LAC promoter, such that expression of the GAL2 gene can be regulated (either increased or decreased). In certain embodiments, the mutation in the GAL2 gene is through operably linking the gene to the inducible or repressible promoter.

Certain methods and compositions employ a yeast cell comprising a mutation in the GAL1 gene. In specific embodiments, the mutation in the GAL1 gene leads to or results in decreased amount of GAL1 available to or the removal of GAL1 from the GAL network in the yeast cell. In certain embodiments, the GAL1 gene is operably linked to an inducible promoter, a constitutive promoter, or a repressible promoter, such as for example, a CUP promoter, a MET promoter, a PHO promoter, and a LAC promoter, such that expression of the GAL2 gene can be regulated (either increased or decreased). In certain embodiments, the mutation in the GAL1 gene is through operably linking the gene to the inducible or repressible promoter.

Certain methods and compositions employ a yeast cell comprising a mutation in one or more of the following genes: GAL4, GAL80, and GAL3. In certain embodiments, each of the mutated genes is operably linked to an inducible promoter or a repressible promoter, such as for example, a CUP promoter, a MET promoter, a PHO promoter, and a LAC promoter, such that expression of the GAL2 gene can be regulated (either increased or decreased). In certain embodiments, the mutation in the GAL4, GAL80, and/or GAL3 genes is through operably linking the gene(s) to the inducible or repressible promoter.

Certain methods and compositions employ a GAL-responsive promoter which responds to a molecule is a galactose or a galactose analog. In certain embodiments, the galactose analog binds GAL3. GAL-responsive promoter responds to the molecule and increases the expression of the nucleic acid. In certain embodiments, a GAL-responsive promoter responds to the molecule and increases the expression of a nucleic acid operably linked to the promoter. In certain embodiments, a GAL-responsive promoter responds to the molecule and decreases the expression of a nucleic acid operably linked to the promoter. In certain embodiments, a GAL-responsive promoter is a native promoter, or a naturally-occurring promoter in yeast cells. Specific embodiments may employ a GAL1 promoter, GAL2 promoter, GAL3 promoter, GAL4 promoter, GAL80 promoter, GAL 1,10 promoter, or any other GAL-responsive promoter. In certain embodiments, a GAL-responsive promoter is a heterologous promoter or a promoter that is not a naturally-occurring promoter in yeast. In certain embodiments, a GAL-responsive promoter comprises one or more GAL4 upstream activation sequences. In certain embodiments, a GAL-responsive promoter is a synthetic promoter comprising one or more GAL4 upstream activation sequences. In certain embodiments, a synthetic promoter further comprises a constitutive promoter linked with the one or more GAL4 upstream activation sequences, and in certain embodiments, the constitutive promoter is activated in response to the molecule. In alternative embodiments, the constitutive promoter is repressed in response to the molecule.

BRIEF DESCRIPTION OF THE DRAWINGS

FIG. 7 is a table showing the genotypes of the engineered strains described in Examples 1-3.

DETAILED DESCRIPTION OF THE INVENTION

1. Overview

Figure 1A:
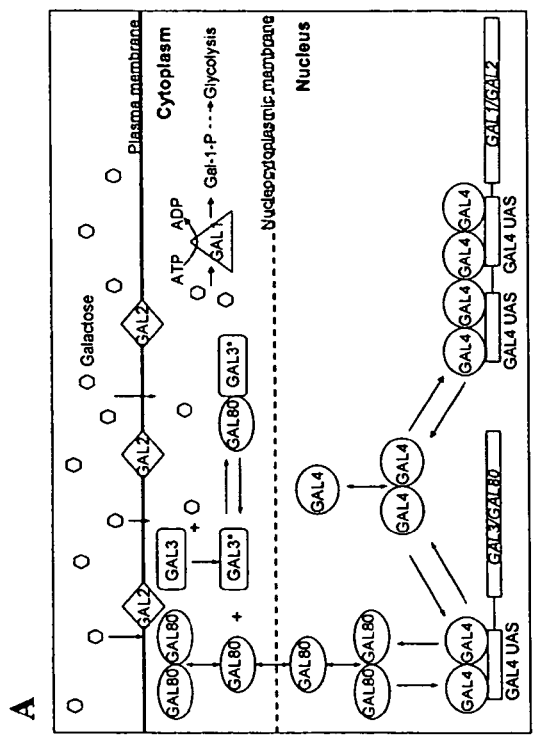
FIGS. 1A-1C are schematic diagrams showing the native GAL network and constructs used to alter and assay network response. A, Schematic of the native GAL network in *S. cerevisiae*. B, Schematic of the nested feedback control loops regulating the response of the GAL network in *S. cerevisiae*. C, General schematic of the constructs used to replace the native promoters of GAL2, GAL3, and GAL80 with tetracycline-repressible promoters.

To provide an overall understanding of the invention, certain illustrative embodiments will now be described, including methods and compositions for regulating the production of a protein or other compound or molecule of interest in yeast. Also provided are yeast cells (e.g., *Saccharomyces cerevisiae* cells) with an engineered Galactose (GAL) network. The engineered networks enable tuning or modulating of the expression of genes in the GAL network. The methods and cells of the invention may be used in a variety of contexts. For example, they may be used to produce compounds or proteins that must be expressed at a specific level. For example, the invention may be utilized to produce proteins that are toxic to a cell when expressed at high levels. In addition, the methods and cells of the invention may be used to study the physiological activity of a protein or compound when expressed at minimal or maximal levels, or when expressed at intermediate levels.

Described herein are yeast cells having an engineered GAL network. As a result of these alterations, the expression response from proteins expressed behind GAL promoters are significantly altered from wild-type response. The wild-type response is characterized by a sharp switch-like induction response over a narrow concentration of the inducer molecule, galactose. In addition, cell populations exhibit all-or-none type characteristics where cells shift between non-induced and fully-induced states.

In contrast to the sharp induction of the GAL network in response to inducing molecules, the methods and cells of the invention allow for linear protein expression from a gene operably linked to a GAL promoter in response to an inducer. In certain embodiments, the invention also provides cells with a tunable GAL network. For instance, in a tunable GAL network, expression of a gene operably linked to a GAL promoter is proportional to the amount of inducer that contacts the cell. In this system, the expression level of a gene operably linked to a GAL promoter displays a linear response that is dependent on the amount of inducer that contacts the cell. In certain other embodiments, the invention provides a GAL network with an increased level of expression of a gene operably linked to a GAL promoter, while retaining the linear expression of the gene in response to an inducer.

In certain embodiments, the invention also provides engineered cells that exhibit increased homogeneity in their cell behavior. For example, a population of cells with an engineered GAL network displays increased homogeneity in the expression of a gene operably linked to a GAL promoter.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

2. Definitions

For convenience, certain terms employed in the specification, examples, and appended claims are collected here. These and other terms are defined and described throughout the application. Unless defined otherwise, all technical and scientific terms used herein have the same meaning as commonly understood by one of ordinary skill in the art to which this invention belongs.

As used herein, the term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

The term "encodes," unless evident from its context, will be meant to include DNA sequences that encode a polypeptide, as the term is typically used, as well as DNA sequences that are transcribed into inhibitory antisense molecules. A "coding region" includes polynucleotide regions that, when present in a DNA form, can be expressed as an RNA molecule. The coding region may encode, for example, a polypeptide produced through translation of the RNA. A coding region may also encode an RNA that is not translated into a polypeptide, such as an RNA aptamer, a ribosomal RNA or other biologically active RNA molecule.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded and double-stranded polynucleotides. This term includes both naturally occurring nucleotide and artificially modified nucleotides.

The terms "peptide," "polypeptide" and "protein" are used interchangeably herein.

By "operably linked" is meant that a gene and transcriptional regulatory sequence(s) are connected in such a way as to permit expression of a DNA sequence in a manner dependent upon factors interacting with the regulatory sequence(s).

The term "promoter" is used herein to refer to any nucleic acid that provides sufficient cis-acting nucleic acid regulatory elements to support the initiation of transcription of an operably linked nucleic acid in the appropriate conditions. Appropriate conditions, also referred to as "inducers" herein, may include the presence or activation of appropriate trans-acting factors, such as an RNA polymerase, a sigma factor, a transcription factor or another compound or molecule that induces transcription. Appropriate conditions may also include the absence or inactivation of negative regulatory factors, such as repressors. Appropriate conditions may further include chemical and physical conditions such as pH and temperature that are compatible with promoter function. Exemplary regulatory elements that may be part of a promoter include sigma factor binding sites (generally in bacterial and bacteriophage promoters), transcription factor binding sites, small molecule binding sites, repressor binding sites, etc. A promoter may be affected by one or more cis-acting or trans-acting element that is external to the promoter. Many promoters are "conditional" or "regulated" meaning that the degree to which the promoter supports the initiation of transcription is affected by one or more conditions inside or outside the cell.

"Transcriptional regulatory sequence" is a generic term used throughout the specification to refer to DNA sequences, such as initiation signals, enhancers, upstream activation sequences (UAS) and promoters and the like which induce or control transcription of coding sequences with which they are operably linked. These sequences can be use to increase, decrease, or maintain a desired level of transcription, including constitutively active, and constitutively inactive.

The term "expression" with respect to a DNA sequence refers to transcription of the DNA sequence and, as appropriate, translation of the resulting mRNA transcript to a protein. Thus, as will be clear from the context, expression of a protein results from transcription and translation of the open reading frame sequence.

As used herein, the term "transformation" is art recognized and refers to the introduction of an exogenous nucleic acid, e.g., an expression vector, into a recipient cell, including eukaryotic and prokaryotic cells, by nucleic acid-mediated gene transfer. Any method can be used to introduce the nucleic acid into the recipient cell. For example, direct uptake, transduction, mating, electroporation, calcium chloride transformation or lipid-mediated transformation may be used.

As used herein, the term "small molecule" refers to a molecule having a molecular weight of less than about 6,000, more preferably a molecular weight of less than about 2,000 and even more preferably a molecular weight of less than about 1,000. Examples of small molecules include, without limitation, drugs, metabolites, intermediates, cofactors, transition state analogs, ions, metals, toxins and natural and synthetic polymers (e.g., proteins, peptides, nucleic acids, polysaccharides, glycoproteins, hormones, receptors and cell surfaces such as cell walls and cell membranes).

The term "vector" refers to a nucleic acid molecule capable of transporting another nucleic acid to which it has been linked. One type of vector is an episome, i.e., a nucleic acid capable of extra-chromosomal replication, such as a plasmid. Another type of vector is an integrative vector that is designed to recombine with the genetic material of a host cell. Vectors may be both autonomously replicating and integrative, and the properties of a vector may differ depending on the cellular context (a vector may be autonomously replicating in one host cell type and purely integrative in another host cell type). Vectors designed to express coding sequences are referred to herein as "expression vectors".

3. Engineered GAL Networks

Figure 1B:
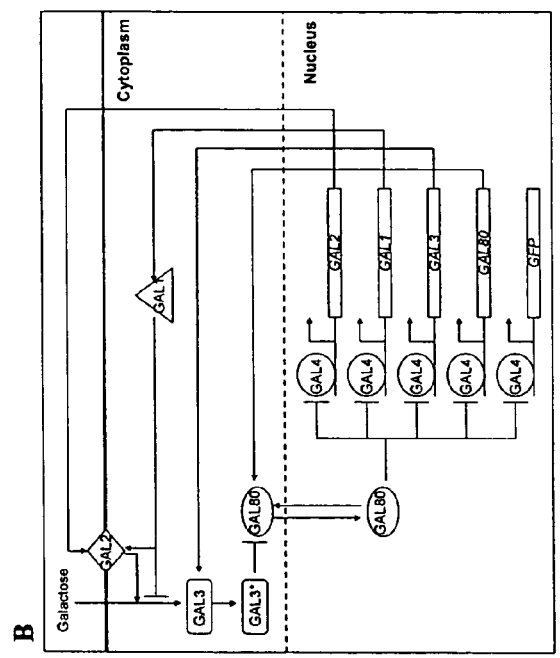

The GAL promoter system is taken from an endogenous metabolic network regulating expression of a number of structural and regulatory genes required for efficient utilization of galactose as a primary carbon source (FIG. 1A). This network has served as a paradigm for gene regulatory circuits in eukaryotic organisms. In noninducing-nonrepressing media, the Gal4p transcriptional activator binds as a dimer to recognition sites upstream of each galactose-regulated gene referred to as upstream activation sites (UASs). An inhibitory protein Gal80p dimerizes and binds to nuclear Gal4p in the absence of galactose, preventing recruitment of activator proteins by Gal4p and effectively repressing gene expression. In the presence of inducer, Gal3p becomes activated and gains affinity for Gal80p, thereby reducing the amount of Gal80p bound to Gal4p and permitting transcription from GAL promoter elements. Gal3p is an exclusively cytoplasmic protein, whereas Gal80p continuously shuttles between the nucleus and cytoplasm and becomes sequestered in the cytoplasm when bound to activated Gal3p (Peng et al. (2002) *Proc. Natl. Acad. Sci. USA* 99, 8548-8553). In the presence of glucose, the same genes are rapidly and fully repressed by multiple mechanisms; the intracellular galactose concentration is reduced via transcriptional repression and catabolite inactivation of Gal2p (Horak et al. (1997) *J. Bacteria* 179, 1541-1549), and the Mig1p repressor inhibits both the transcription and activity of Gal4p (Lamphier et al. (1992) *Proc. Natl. Acad. Sci. USA* 89, 5922-5926 and Nehlin et al. (1991) *EMBO J.* 10, 3373-3377). The inducer molecule galactose is transported across the cell membrane by both a facilitated diffusion mechanism and a galactose permease protein Gal2p, which has both a high-affinity and low-affinity galactose transport mechanism (Ramos et al. (1989) *J. Bacteriol.* 171, 3539-3544). Galactose is utilized as a sugar source by the cell through an initial conversion step catalyzed by a galactokinase Gal1p (Schell et al. (1977) J. Biol. Chem. 252, 1162-1166). The levels of Gal2p, Gal3p, and Gal80p are regulated by GAL promoters, thereby forming three nested feedback control loops (FIG. 1B) (Acar et al. (2005) *Nature* 435, 228-232). A number of other structural and regulatory proteins are under the control of GAL promoters with either one or two UASs.

In certain embodiments, the invention provides a yeast cell comprising a GAL network that is engineered to provide linear and/or tunable expression of a protein or compound of interest. Such engineered networks may be used, for example, to regulate the production of a protein or compound of interest. In one embodiment, the GAL network comprises a mutation in the GAL2 gene and a nucleic acid encoding a protein of interest operably linked to a promoter that responds to an inducer molecule. As used herein, the term "mutation" refers to nucleic acid alterations, such as one or more nucleotide substitutions, additions, or deletions, that alter the wild type activity of a gene. Mutations may also include duplications, inversions, or deletions of a region of DNA. A mutation in the GAL2 gene may alter expression of the nucleic acid, such that expression of the nucleic acid responds in a more linear manner to changes in inducer molecule levels. For instance, contacting the cell with a greater amount of the inducer results in a greater amount of expression of the nucleic acid. In another embodiment, an engineered GAL network comprises a mutation in the GAL1 and GAL2 genes, and a nucleic acid encoding a protein of interest operably linked to a promoter that responds to an inducer. Such yeast cells may be used, for example, to express the nucleic acid at increased levels relative to cells that comprise a wild type GAL1 gene.

A yeast cell that comprises an engineered GAL network (e.g., cells with a mutation in the GAL2 and/or GAL1 genes) may be used to regulate the production of a protein or compound of interest. The production of the protein or compound of interest may be direct or indirect. For example, a protein of interest is directly produced when a nucleic acid encoding for the protein of interest is operably linked to a promoter that responds to an inducer. Alternatively, a protein or compound of interest may be indirectly produced if the nucleic acid encodes a protein that is an intermediary protein that affects the production of the protein or compound of interest (e.g., a transcription factor or other factor necessary for activation of the protein or compound of interest).

In certain embodiments, an inducible promoter is operably linked to a nucleic acid that encodes a protein of interest, or to a nucleic acid that encodes a protein that is an intermediary protein in the production of a protein or compound of interest. Preferably, a nucleic acid encoding a protein of interest is operably linked to an inducible promoter. A variety of inducible promoters may be used according to the invention described herein. The selection of appropriate promoter may depend on the host cell being used, and may be determined by the skilled artisan. For example, in the yeast S. cerevisiae, any of the promoters that respond to the presence of the galactose inducer or its analog may be used. Examples of galactose-dependent promoters include, without limitation, the GAL1, GAL2, GAL3, GAL4, PGM2, LAP3, GAL7, GAL10, GAL11, SIN4, GAL80, and GAL83 promoters. In certain embodiments, a promoter, a native galactose-dependent promoter or a synthetic promoter, comprising the GAL4 UAS sequence is operably linked to a nucleic acid that encodes a protein of interest, or to a nucleic acid that encodes a protein that is an intermediary protein in the production of a protein or compound of interest.

Certain embodiments of the invention employ other promoters, such as for example inducible promoters. In certain embodiments, such inducible promoters are employed to modulate the expression of regulatory proteins of the GAL network in a yeast cell. Examples of other inducible promoters that may be used in the invention include, without limitation, tetracycline and tetracycline analog-responsive promoters (e.g., tetO promoters such as $tetO_2$ and $tetO_7$), methinone-responsive promoters (e.g., MET promoters such as MET25), phosphate-responsive promoters (e.g., PHO promoters), CUP promoters (e.g., CUP1) that respond to the presence of copper or silver ions, or the E. coli lac promoter. Other inducible promoters that may be appropriate based on the host cell used include, but are not limited to, $Zn^{2+}$ metallothionein promoter, metallothionein-1 promoter, human metallothionein IIA promoter, mouse mammary tumor virus early promoter, mouse mammary tumor virus LTR promoter, triose dehydrogenase promoter, herpes simplex virus thymidine kinase promoter, simian virus 40 early promoter, and retroviral myeloproliferative sarcoma virus promoter. In certain other embodiments, a constitutive promoter may be used. For example, constitutive promoters that may be used for gene expression in S. cerevisiae include, for example, promoters for any of the following S. cerevisiae genes: alcohol dehydrogenase (ADH) genes which are involved in ethanol metabolism (e.g., ADH1, ADH2, ADH3, ADH4, or ADH5); glycerol-3-phosphate (GPD) genes which are involved in glycerol synthesis (e.g., GPD1 or GPD2); TEF1, TEF2, YEF3, CAM1, TEF4, or EFB1, which are involved in translation; or any of the CYC genes, such as CYC1, CYC2, CYC3, CYC7, or CYC8. Other examples of constitutive promoters that may be appropriate based on the host cell used include, but are not limited to, cytomegalovirus promoter (CMV), SV40 early promoter, Rous Sarcoma Virus (RSV) promoter, phosphoglycerate kinase promoter (PGK), and chicken beta-actin promoter (CBA) (Hamer et al., J. Mol. Appl. Gen. 1:273 (1982); McKnight, Cell 31:355 (1982); Benoist et al., Nature (London) 290:304 (1981); (Foecking et al., Gene 45:101 (1980); Johnston, et al., Proc. Natl. Acad. Sci. (USA) 79:6971 (1982); and, Silver, et al., Proc. Natl. Acad. Sci. (USA) 81:5951 (1984)). Suitable promoters for use in prokaryotic host cells include, but are not limited to, promoters capable of recognizing the T4, T3, Sp6 and T7 polymerases, the $P_R$ and $P_L$ promoters of bacteriophage lambda, the trp, recA, heat shock, and lacZ promoters of E. coli, the .alpha.-amylase and the .sigma.-specific promoters of B. subtilis, the promoters of the bacteriophages of Bacillus, Streptomyces promoters, the int promoter of bacteriophage lambda, the bla promoter of the .beta.-lactamase gene of pBR322, and the CAT promoter of the chloramphenicol acetyl transferase gene. Prokaryotic promoters are reviewed by Glick, J. Ind. Microbiol. 1:277 (1987); Watson et al., MOLECULAR BIOLOGY OF THE GENE, 4th Ed., Benjamin Cummins (1987); Ausubel et al., supra, and Sambrook et al., supra.

Expression of a nucleic acid that is operably linked to an inducible promoter is dependent on the presence of the promoter's cognate inducer molecule. For example, expression from a tetracycline promoter is increased in the presence of tetracycline or tetracycline analog, such as doxycycline. Expression from a methionine-responsive promoter is increased in the presence of methionine. Expression from a CUP promoter is increased in the presence of copper or silver ions. Expression from a lac promoter is increased in the presence of IPTG. Other promoter sequences are known to one of skill in the art. See for example, Schleif, R. (1992) in Transcriptional Regulation (CSHL Press, Cold Spring Harbor, NIA, pp. 643-665.

The present invention may be used for the production of any protein or compound, so long as the protein or compound can be suitably expressed by a host cell. For example, the present invention may be used to produce natural and synthetic polymers that are native or heterologous to the host cell, including proteins, peptides, nucleic acids, polysaccharides, glycoproteins, hormones or sterols, enzymes, or small molecules, such as drugs, metabolites, intermediates, cofactors, transition state analogs, ions, metals, nucleic acids, and toxins. In a specific embodiment, the invention provides methods and compositions for regulating the production of native or heterologous organic molecules, including but not limited, alkaloids, terpenes and terpenoids, alkanes, alkenes, alkynes, dienes, isoprenes, long chain alcohols, long chain aldehydes, long chain carboxylic acids, surfactants, wax esters and combinations thereof. Organic molecules may be saturated or unsaturated.

Heterologous DNA sequences encoding a protein of interest may be obtained in various ways. For example, DNA sequences may be obtained from database (public or proprietary) searching using query sequences, or through genome sequencing and sequence homology comparison. Sequence homology searching is routine in modern biology, while genome sequences of the source organism may be routinely obtained through whole genome sequencing. DNA sequences may also be identified using standard molecular biological techniques, such as, for example, hybridization assays using a nucleic acid that is homologous to the nucleic acid of interest. A nucleic acid can be produced synthetically or may be obtained using cloning and recombinant DNA techniques known in the art.

In other embodiments, the present invention provides a population of yeast cells that is characterized by a more homogeneous level of expression of a gene operably linked to a promoter that responds to an inducer. The yeast cells in such a population comprise a mutation in the GAL2 gene.

Any microorganism that is amenable to genetic engineering may be used as a host cell in the invention. Preferably, microbes that possess genetic pathways that are structurally or functionally homologous to the GAL network in *S. cerevisiae* are used. In certain embodiments, the GAL network in *S. cerevisiae* is utilized in the invention. In other embodiments, other yeast cells are used. For instance, yeasts such as *Pichia stipitis, Candida boidinii, Hansenula polymorpha, Pichia methanolica, Pichia pastoris, Kluveromyces lactis, Schwanniomyces occidentalis*, and *Yarrowia lipolytica* may be used in the invention. In certain embodiments, a GAL network may be genetically engineered into a host cell, such as for example, a yeast cell.

4. Expression Constructs

A nucleic acid encoding a protein of interest and operably linked to an inducible promoter may be incorporated into a vector or may be integrated into the genome of the host organism. In certain embodiments, a nucleic acid encoding a protein of interest and operably linked to an inducible promoter is incorporated into a vector suitable for expression in either prokaryotic cells, eukaryotic cells (yeast, avian, insect or mammalian), or both. A vector may have sequence information that allows it to be propagated in a host cell. For example, a vector comprising a nucleic acid construct disclosed herein may be a plasmid for use with a eukaryotic cell such as a yeast cell. Such a plasmid will generally contain an origin of replication or other sequence that allows it to be propagated within the host cell. A plasmid or other vector may also be designed to integrate into a chromosome of a host cell. The plasmid may optionally contain a replication sequence that allows the plasmid to be replicated in a bacterial host cell, such as *E. coli*. The manipulation of plasmid or other vector DNA is well known to one of skill in the art (Sambrook, J.; Fritsch, E. F.; Maniatis, T. Molecular Cloning, A Laboratory Manual; 2nd ed.; Cold Spring Harbor Laboratory Press: 1989). Other common vectors include viral vectors, containing at least some portion of a viral genome that assists in replication and/or integration of the vector in a host cell, and transposon vectors, containing at least some portion of a transposon (typically one or more terminal repeat sequences) that assists in replication and/or integration of a transposon in a host cell. In another embodiment, the nucleic acid construct is RNA and is introduced into the cell directly as RNA.

Expression vehicles for production of a protein or compound of interest include plasmids and other vectors. For instance, suitable vectors for the expression of a nucleic acid encoding a protein of interest include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Mammalian expression vectors may contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below. The various methods employed in the preparation of the plasmids and transformation of host organisms are well known in the art.

For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17.

Various viral vectors can be utilized for introducing a nucleic acid encoding a protein of interest into cells. These viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicularstomatitis virus), paramyxovirus (e.g. measles and Sendai), positive strand RNA viruses such as picornavirus and alphavirus, and double stranded DNA viruses including adenovirus, herpes virus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus. and hepatitis virus, for example.

For example, a retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) may be utilized.

Other vectors include those suitable for expression in a yeast cell. For example, various expression vectors suitable for the yeast system are commercially available (e.g., Invitrogen™).

Shuttle vectors between yeast cells and *E. coli* cells may also be employed, such as for example, the shuttle vector in Rhodes et al., Plasmid (1990) 23(2):159-62.

Methods of constructing the vectors containing a nucleic acid encoding a protein of interest are well known in the art (see, e.g., Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997)). For example, the nucleic acid elements can be isolated from nature, modified from native sequences or manufactured de novo (e.g., by chemical synthesis or recombinant DNA/RNA technology). These elements can then be isolated and ligated together by methods known in the art, such as exploiting and manufacturing compatible cloning or restriction sites. Methods for integrating nucleic acid into the host genome are also known in the art. For example, a nucleic acid encoding a protein of interest may be integrated into the host genome by homologous recombination.

In certain embodiments, one or more nucleic acids of the invention are introduced into a host cell. A host cell is any cell capable of being cultured. Particularly preferred host cells include, but are not limited to yeast cells, such as *Saccharomyces cerevisiae, Pichia stipitis, Candida boidinii, Hansenula polymorpha, Pichia methanolica, Pichia pastoris, Kluveromyces lactis, Schwanniomyces occidentalis*, and *Yarrowia lipolytica*. Yeasts are particularly suitable for the production of a protein or compound of interest. These microbes offer the ease of microbial growth and gene manipulation, while able to perform eukaryotic-specific post-translational modifications (e.g., proteolytic processing, folding, disulfide bridge formation and glycosylation). Host cells may also include bacteria, such as *E. coli, B. subtilis, Streptomyces antibioticus, Streptomyces mycarofaciens, Streptomyces avenmitilis, Streptomyces caelestis, Streptomyces tsukubaensis, Streptomyces fradiae, Streptomyces platensis*,

*Streptomyces violaceoniger, Streptomyces ambofaciens, Streptomyces griseoplanus,* and *Streptomyces venezuelae.* Host cells may also be mammalian (e.g. CHO cells, fibroblasts, human embryonic kidney cells, adult or embryonic stem cells, hepatic cell lines, etc.), invertebrate (e.g. insect cells suitable for baculovirus-mediated gene expression, nematode cells) or plant cells.

Nucleic acids may be introduced into host cells according to any method known in the art, including, for example, electroporation, tungsten particle bombardments (typically with plants and algae), calcium chloride mediated transformation, viral infection, lipofection, calcium phosphate precipitation, microinjection, and DEAE-dextran mediated transfection. Such methods are described in more detail, for example, in Sambrook et al., Molecular Cloning: A Laboratory Manual, Second Edition, Cold Spring Harbor University Press, New York (1989); and Ausubel, et al., Current Protocols in Molecular Biology, John Wiley & Sons, New York (1998), the teachings of which are incorporated herein by reference. The nucleic acids may be introduced stably or transiently into the host cell. For stable transformation, a DNA sequence will generally further comprise a selectable marker. Useful vectors will generally contain a selectable marker gene. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, chloramphenical, kanamycin or tetracycline, (b) complement auxotrophic deficiencies, or (c) supply critical nutrients not available from complex media, e.g., the gene encoding D-alanine racemase for Bacilli.

5. Detection and Analysis of Gene Products

Any of the standard analytical methods, such as gas chromatography-mass spectrometry, and liquid chromatography-mass spectrometry, HPLC, capillary electrophoresis, Matrix-Assisted Laser Desorption Ionization time of flight-mass spectrometry etc., may be used to analyze the levels and the identity of a protein or compound produced as described herein.

In certain embodiments, the assay will be set up to directly detect, by chemical or photometric techniques, a molecular species which is produced in the engineered host cell. Such a molecular species' production must be dependent, at least in part, on expression of the nucleic acid encoding the protein of interest or encoding an intermediary protein. In other embodiments, the detection step of the subject method involves characterization of fractionated media/cell lysates (the test extract), or application of the test extract to a biochemical or biological detection system. In other embodiments, the assay indirectly detects the formation of products of a heterologous pathway by observing a phenotypic change in the host cell.

In certain embodiments, analogs related to a known class of compounds will be sought, as for example analogs of alkaloids, aminoglycosides, ansamacrolides, beta-lactams (including penicillins and cephalosporins), carbapenems, terpenoids, prostanoid hormones, sugars, fatty acids, lincosaminides, macrolides, nitrofurans, nucleosides, oligosaccharides, oxazolidinones, peptides and polypeptides, phenazines, polyenes, polyethers, quinolones, tetracyclines, streptogramins, sulfonamides, steroids, vitamins and xanthines. In such embodiments, if there is an available assay for directly identifying and/or isolating the natural product, and it is expected that the analogs would behave similarly under those conditions, the detection step of the subject method can be as straight forward as directly detecting analogs of interest in the cell culture media or preparation of the cell. For instance, chromatographic or other biochemical separation of a test extract can be carried out, and the presence or absence of an analog detected, e.g., spectrophotometrically, in the fraction in which the known compounds would occur under similar conditions. In certain embodiments, such compounds can have a characteristic fluorescence or phosphorescence which can be detected without any need to fractionate the media and/or recombinant cell.

In related embodiments, whole or fractionated culture media or lysate from a recombinant host cell can be assayed by contacting the test sample with a heterologous cell ("test cell") or components thereof. For instance, a test cell, e.g., which can be prokaryotic or eukaryotic, is contacted with conditioned media (whole or fractionated) from a recombinant host cell, and the ability of the conditioned media to induce a biological or biochemical response from the target cell is assessed. For instance, the assay can detect a phenotypic change in the target cell, as for example a change in: the transcriptional or translational rate or splicing pattern of a gene; the stability of a protein; the phosphorylation, prenylation, methylation, glycosylation or other post translational modification of a protein, nucleic acid or lipid; the production of 2nd messengers, such as cAMP, inositol phosphates and the like. Such effects can be measured directly, e.g., by isolating and studying a particular component of the cell, or indirectly such as by reporter gene expression, detection of phenotypic markers, and cytotoxic or cytostatic activity on the test cell.

When screening for bioactivity of test compounds produced by the recombinant host cells, intracellular second messenger generation can be measured directly. A variety of intracellular effectors have been identified. For instance, for screens intended to isolate compounds, or the genes which encode the compounds, as being inhibitors or potentiators of receptor- or ion channel-regulated events, the level of second messenger production can be detected from downstream signaling proteins, such as adenylyl cyclase, phosphodiesterases, phosphoinositidases, phosphoinositol kinases, and phospholipases, as can the intracellular levels of a variety of ions.

In still other embodiments, the detectable signal can be produced by use of enzymes or chromogenic/fluorescent probes whose activities are dependent on the concentration of a second messenger, e.g., such as calcium, hydrolysis products of inositol phosphate, cAMP, etc. Reporter genes may also be operably linked to an inducible promoter to gene expression activity in response to an inducer molecule.

Many reporter genes and transcriptional regulatory elements are known to those of skill in the art and others may be identified or synthesized by methods known to those of skill in the art. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368); β-lactamase, GST, or Green Fluorescent Protein or analogs.

In still other embodiments, the detection step is provided in the form of a cell-free system, e.g., a cell-lysate or purified or semi-purified protein or nucleic acid preparation. The sample obtained from the host cell can be tested for such activities as inhibiting or potentiating such pairwise complexes (the "target complex") as involving protein-protein interactions, protein-nucleic acid interactions, protein-ligand interactions, nucleic acid-nucleic acid interactions, and the like. The assay can detect the gain or loss of the target complexes, e.g., by endogenous or heterologous activities associated with one or both molecules of the complex.

Assays which are performed in cell-free systems, such as may be derived with purified or semi-purified proteins, are often preferred as "primary" screens in that they can be generated to permit rapid development and relatively easy detection of an alteration in a molecular target when contacted with a test sample. Detection and quantification of the pairwise complexes provides a means for determining the test samples efficacy at inhibiting (or potentiating) formation of complexes. The efficacy of the compound can be assessed by generating dose response curves from data obtained using various concentrations of the test sample. Moreover, a control assay can also be performed to provide a baseline for comparison. For instance, in the control assay conditioned media from untransformed host cells can be added.

The amount of target complex may be detected by a variety of techniques. For instance, modulation in the formation of complexes can be quantitated using, for example, detectably labeled proteins or the like (e.g. radiolabeled, fluorescently labeled, or enzymatically labeled), by immunoassay, or by chromatographic detection.

In still other embodiments, a purified or semi-purified enzyme can be used as to assay the test samples. The ability of a test sample to inhibit or potentiate the activity of the enzyme can be conveniently detected by following the rate of conversion of a substrate for the enzyme. Alternatively, the activity of the protein of interest can be detected by assaying its activity in the presence of a provided substrate.

A protein or compound of interest may also be isolated from one or more components of the host cell sample. Samples may be processed by any means known in the art that renders the protein or compound of interest available for assaying in the methods described herein. Methods for processing samples include, but are not limited to, mechanical, chemical, or molecular means of lysing and/or purifying cells and cell lysates. Processing methods may include, for example, chromatographic methods such as ion exchange (e.g., cation and anion), size exclusion, gel filtration, affinity, and hydrophobic interaction chromatography, or ultrafiltration, electrophoresis, and immunoaffinity purification with antibodies specific for particular epitopes of the polypeptide.

EXAMPLES

The invention now being generally described, it will be more readily understood by reference to the following examples, which are included merely for purposes of illustration of certain aspects and embodiments of the present invention, and are not intended to limit the invention.

Example 1

Regulation of the GAL Network in Galactose Permease-Deficient Cells

Galactose Permease Deletion Results in a Linear Induction Response

Figures 2A, 2B:
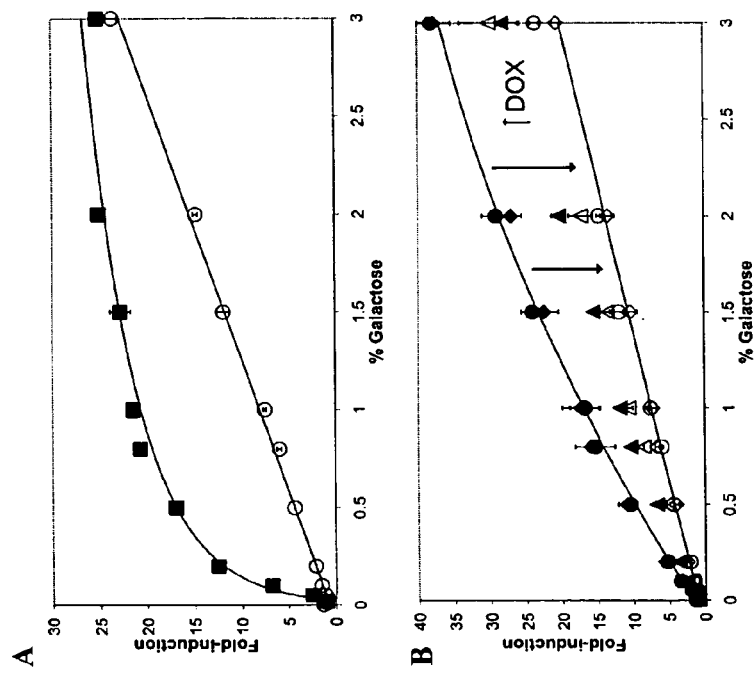
FIGS. 2A and 2B are graphs showing the population-averaged response from strains with altered Gal2p regulation. A, Population-averaged response of the Gal2p deletion strain (gal2Δ) (open circles) and the wild-type strain (filled squares). B, Population-averaged response of the constitutive Gal2p strain (tetO$_2$: GAL2) at various concentrations of doxycycline. Levels of Gal2p decrease with increasing concentrations of doxycycline with full repression at concentrations over 1 µg/ml; no doxycycline (filled diamonds), 5 ng/ml (filled circles), 25 ng/ml (filled triangles), 50 ng/ml (open triangles), 5 µg/ml (open diamonds), and gal2Δ strain (open circles).

Galactose is transported into the cell through both an induced high-affinity and low-affinity transport mechanism and an uninduced facilitated diffusion mechanism. The response of the GAL network was determined when the outermost positive feedback loop controlling the autocatalytic expression of the galactose permease Gal2p was removed. Initial studies examined the response of the network in the absence of the induced transport response. A GAL2 deletion strain was constructed by inserting a kanamycin resistance marker into the GAL2 locus of the chromosome. This system enabled the examination of the network response under conditions where the transport of galactose is limiting. Transcriptional activation, or the level of Gal4p not bound by Gal80p, in both the gal2Δ and the wild-type strain was determined by measuring fluorescence levels in cells harboring yEGFP under the control of a GAL1 promoter, which harbors two UASs. The data from these studies indicate that the steady-state population-averaged induction response is linear with respect to galactose in the gal2Δ strain across a wide range of inducer concentrations, whereas the wild-type strain demonstrates the expected autocatalytic response curve. As illustrated in FIG. 2A, both strains exhibit similar induction levels of approximately 25-fold over uninduced cells at the highest concentration of three percent galactose.

This demonstrates that the positive feedback loop regulating the expression of Gal2p is necessary for the sharp, autocatalytic response of the system to galactose observed in the wild-type strain. In the gal2Δ strain, galactose and its non-phosphorylatable analogs are transported solely by an uninduced facilitated diffusion mechanism (Ramos et al. (1989) *J. Bacteria* 171, 3539-3544). One potential explanation is that under these conditions transport effects limit the intracellular galactose concentration and the ensuing network response. Specifically, there will be fewer molecules of galactose to activate Gal3p such that more Gal80p remains bound to Gal4p and therefore a decrease in the transcriptional activation response is observed. This is in contrast to the wild-type environment, where the amount of galactose in the cells increases sharply over a narrow concentration range once galactose gets into the cells as a result of the positive feedback loop regulating Gal2p.

Constitutive Expression of the Galactose Permease Results in a Tunable Linear Response The complete removal of the induced transport mechanism eliminated the switch-like response of the GAL network. The response of the network in the presence of the inducible high- and low-affinity transport mechanisms removed from their feedback regulation scheme was also determined. A constitutive GAL2 strain, tetO$_2$:GAL2, was constructed to allow for tunable levels of Gal2p while removing the native positive feedback control loop. A cassette was constructed to replace the GAL2 promoter with a tetracycline-repressible promoter (Yen et al. (2003) *Yeast* 20, 1255-1262). This cassette, which also contained the tTA transactivator and a kanamycin resistance gene, was inserted into the GAL2 promoter region of the chromosome. Prior studies have indicated that in the absence of an appropriate tetracycline analog such as doxycycline, the expression levels from this promoter are approximately 10-20% of those observed from a fully induced GAL1 promoter (Gari et al. (1997) *Yeast* 13, 837-848 and Belli et al. (1998) *Nucleic Acids Res.* 26, 942-947). Similar steady-state assays of transcriptional activation in these strains were performed under varying concentrations of galactose and doxycycline. The former was expected to modulate the response of the GAL network in the presence of a constant level of galactose transporter, whereas the latter was expected to modulate the level of the galactose transporter. In the absence of doxycycline, permitting high Gal2p expression, the resulting induction curve shifted upward compared to the gal2Δ strain but largely retained linearity (FIG. 2B). Addition of varying concentrations of doxycycline shifted the response curve to lower response levels, while at concentrations of 5 μg/ml Gal2p expression was fully repressed and demonstrated a response identical to that of the gal2Δ strain. In addition, the maximum induction level observed in the tetO$_2$:GAL2 strain was significantly greater than that observed in the wild-type strain, potentially due to the removal of the negative feedback loop on the regulation of Gal2p from increased levels of Gal80p. It should be noted that at high Gal2p expression levels and low galactose concentrations the response of the system is slightly nonlinear, indicating that at low galactose concentrations the high-affinity transport mechanism is dominant and inducer transport is not a limiting factor in GAL promoter activation.

Constitutive Expression of Regulatory Proteins Enhances the Switch-Like Response of the Network The GAL network is regulated by three nested feedback control loops. The Gal2p loop is the exterior feedback loop and the data in the previous Examples indicate that removal of this loop is sufficient for modulating the sharp native response of this network to a linear response. The effects of the two interior nested loops regulating the expression of Gal80p and Gal3p on the steady-state population-averaged response of the GAL network were determined. Separate constitutive Gal80p and Gal3p strains were constructed by replacing the GAL80 and GAL3 promoters with previously described tetracycline-repressible promoter cassettes harboring the his5$^+$ and kanamycin selection markers, respectively. In addition, a combined constitutive Gal80p/Gal3p strain was constructed by sequential insertion of these cassettes into the wild-type strain. These systems enabled the examination of the response of the GAL network under conditions where the two internally nested control loops regulating the transcriptional repressor and activator were individually and combinatorially removed. Similar steady-state population-averaged assays of transcriptional activation in these strains were performed under varying concentrations of galactose and doxycycline.

Figure 3A:
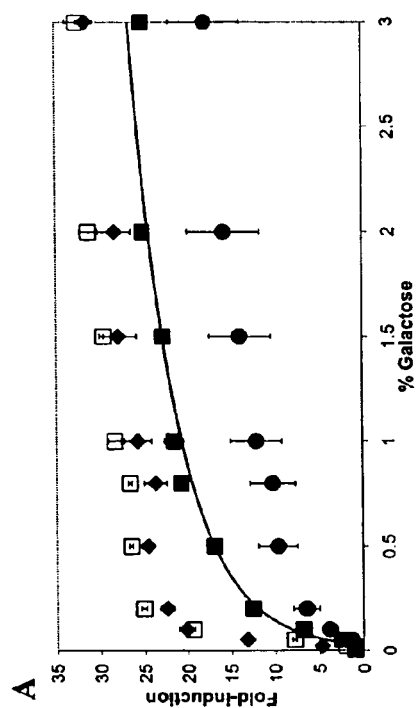
FIGS. 3A-3C are graphs showing the population-averaged response from strains with altered Gal3p and Gal80p regulation. A, Population-averaged response of the wild-type strain (filled squares) and constitutive Gal3p strain (tetO$_2$: GAL3) at nonrepressed conditions (filled diamonds, 0 µg/ml doxycycline), fully repressed conditions (open squares, 5 µg/ml doxycycline), and fully repressed conditions grown overnight in doxycycline (filled circles, 5 µg/ml doxycycline). B, Population-averaged response of the wild-type strain (filled squares) and constitutive Gal80p strain (tetO$_2$: GAL80) at nonrepressed conditions (filled diamonds), repressed conditions (open squares), and repressed conditions grown overnight in doxycycline (filled circles). C, Population-averaged response of the constitutive Gal3p, Gal80p strain (tetO$_2$: GAL3 tetO$_2$: GAL80) at nonrepressed conditions (filled diamonds), repressed conditions (open squares), and repressed conditions grown overnight in doxycycline (filled circles). The inset illustrates induction levels relative to the wild-type strain (filled squares).
Figures 3B, 3C:
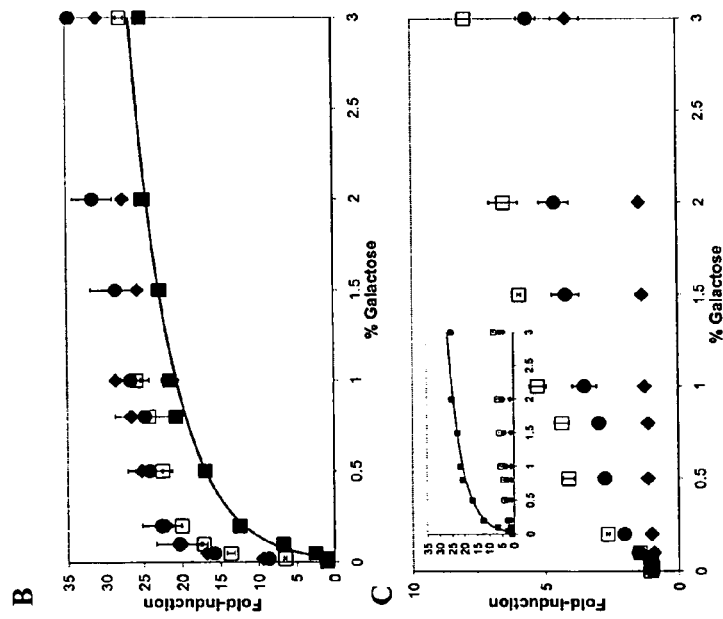

Constitutive strains for either regulatory protein Gal3p or Gal80p did not produce the same linear response observed from the constitutive Gal2p strain. The tetO$_2$:GAL3 strain exhibited a steeper response curve under nonrepressed conditions (FIG. 3A). In addition, the repressed response curve demonstrated a memory response such that when doxycycline and galactose were added at the same time point, the response was similar to that under the nonrepressed conditions, whereas when cells were grown in the presence of doxycycline prior to galactose addition the overall response curve was much lower. The tetO$_2$: GAL80 strain also exhibited a steeper response curve under nonrepressed conditions (FIG. 3B). However, the addition of doxycycline either prior to or at the same time as the addition of galactose did not significantly alter the induction response. In addition, the induction response from the Gal3p/Gal80p constitutive strain was much lower than any of the other strains (FIG. 3C). In this strain a history-dependent response was also observed in the repressed response curve such that slightly higher induction levels were observed when doxycycline and galactose were added at the same time point versus when the cells were grown in doxycycline prior to induction.

Example 2

Examination of the Role of the GAL1p Galactokinase on the Response of the GAL Network Galactokinase Deletion Results in a Regimed Network Response The previous examples indicate that the nested positive and negative feedback loops in the GAL network influence the steady-state induction response to varying levels of galactose. The galactokinase Gal1p is also anticipated to play a key regulatory role in the response of the network as a result of its two distinct activities. The immediate role of this enzyme is in converting galactose into an energy source for the cell. Therefore, it is anticipated that removal of this activity will increase the overall response of the network at a given galactose concentration as the intracellular levels of galactose available for activating Gal3p will be effectively higher. Prior work has demonstrated higher fully induced response levels in a Gal1p knockout strain (Stagoj et al. (2005) *FEMS Microbiol. Lett.* 244, 105-110). However, the galactokinase also plays a key role in the high-affinity transport mechanisms associated with Gal2p (Ramos et al. (1989) *J. Bacteriol.* 171, 3539-3544). To examine the role of the galactokinase on the response of the GAL network, Gal1p deletion strains were constructed in the three different Gal2p regulatory strains: wild-type, gal2Δ, and tetO$_2$:GAL2. gal1Δ strains were constructed by inserting a His3MX6 selection marker into the GAL1 locus of the chromosome. These systems enable examination of the effects of the galactokinase in the response of the system under conditions where the normal Gal2p feedback control is present, Gal2p is present but the feedback control loop is removed, and in the absence of Gal2p. Similar steady-state population-averaged assays of transcriptional activation in these strains were performed under varying concentrations of galactose.

Figure 4:
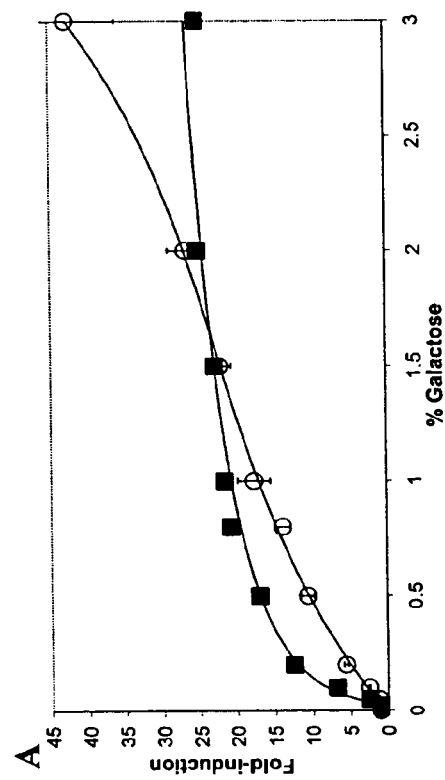
FIGS. 4A-4C are graphs showing the population-averaged response from strains with no Gal1p activity. A, Population-averaged response of the Gal1p deletion strain (gal1Δ) (open circles) and the wild-type strain (filled squares). B, Population-averaged response of the Gal1p deletion, constitutive Gal2p strain (gal1Δ tetO$_2$: GAL2) (open circles) and the corresponding isogenic strain (tetO$_2$: GAL2) (filled squares). C, Population-averaged response of the Ga1p, Gal2p deletion strain (gal1Δ gal2Δ) (open circles) and the corresponding isogenic strain (gal2Δ) (filled squares).
Figures 4B, 4C:
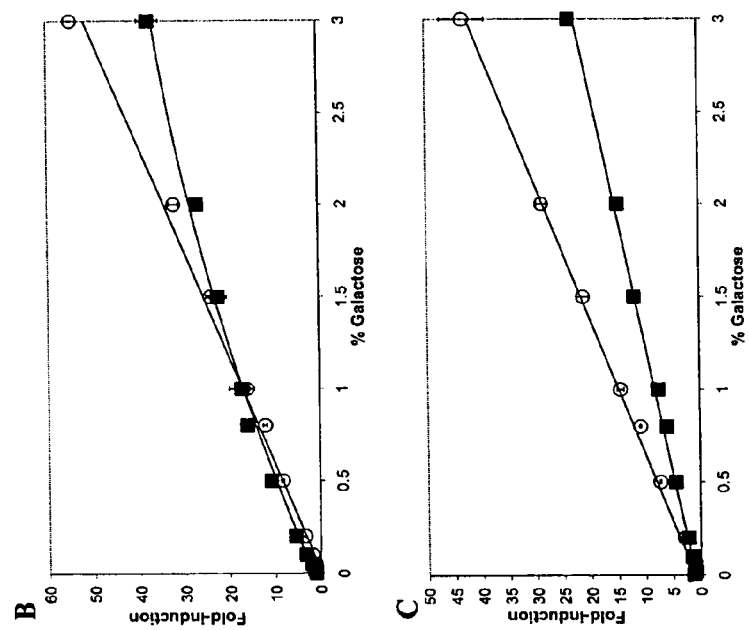

The effects of deleting Gal1p were dependent on strain background and galactose concentration. For instance, in both the gal1Δ and the gal1Δ tetO$_2$: GAL2 strains the induction response exhibited a more linear response in comparison to their respective GAL1 isogenic strains (FIGS. 4A, B). The response can be broken up into two different regimes: the low galactose regime, where the Gal1p deletion strains exhibit a lower induction response relative to their isogenic strains, and the high galactose regime, where the Gal1p deletion strains exhibit a higher induction response that increases linearly with galactose concentration relative to their isogenic strains. In the absence of Gal2p the deletion of Gal1p results in a different induction pattern (FIG. 4C). The response of the gal1Δ gal2Δ strain exhibits only one regime across all galactose concentrations, where the response curve maintains its linear response and is shifted upward from its isogenic strain across all galactose concentrations.

Example 3

Modifications in the GAL Network Affect Cell Population Homogeneity

Population Distributions in GAL2-Modified Strains Exhibit Graded Responses

Figure 5:
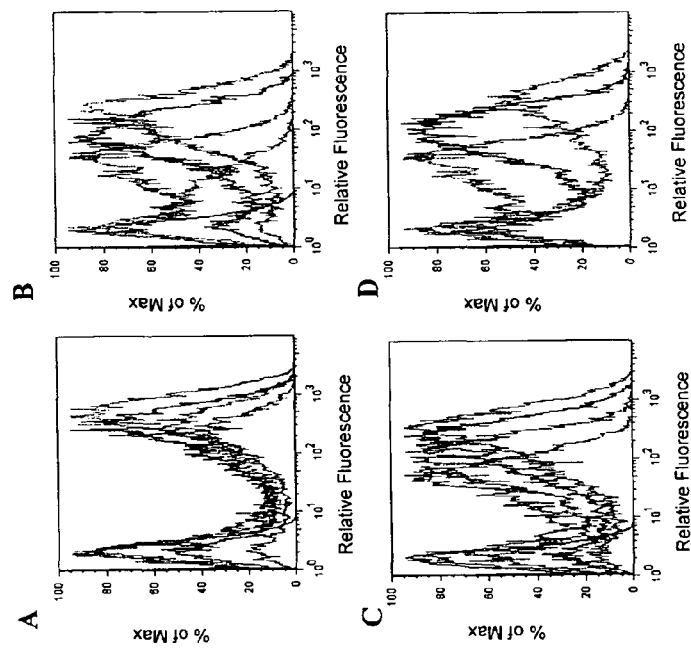
FIGS. 5A-5D are graphs showing the population response from strains with altered Gal2p regulation. For panels A, B, and C galactose concentration is indicated in five curves, from left to right, as 0%, 0.2%, 0.5%, 1%, and 3%. A, Population distribution of cells with the native Gal2p positive feedback control loop (wild-type) across various concentrations of galactose. B, Population distribution of cells with constitutive Gal2p levels (tetO$_2$:GAL2) under nonrepressed conditions (0 µg/ml doxycycline) across various concentrations of galactose. C, Population distribution of cells with no Gal2p (gal2Δ) across various concentrations of galactose. D, Population distributions in 0.5% galactose of wild-type cells exhibiting feedback Gal2p control (left most curve), tetO$_2$:GAL2 cells exhibiting constitutive Gal2p control (middle curve), and gal2Δ cells where Gal2p is absent from the network (right most curve).

Alteration of the regulatory schemes at various control points modifies the steady-state population-averaged response of the GAL network. The effects of these targeted alterations on the population response of the network were determined. Flow cytometry was used to analyze the response of the cell population to alterations in Gal2p regulation. Wild-type, gal2Δ, and tetO$_2$:GAL2 cells were cultured under the same conditions as the population-averaged studies prior to preparation for analysis. The wild-type strain exhibited two distinct populations of fully induced and uninduced cells (FIG. 5A). In accordance with the all-or-none effects observed in other inducible promoter systems (Louis et al. (2002) *Sci. STKE* 2002, PE33), the percentage of fully induced cells increases with increasing galactose concentrations. While both GAL2-modified strains, gal2Δ and tetO$_2$: GAL2, exhibited a significant uninduced or negative population, they did not exhibit the all-or-none effect observed with the wild-type strain. Specifically, the average level of GFP expression from the induced population and the number of cells that were induced increased with galactose concentration (FIGS. 5B, C). This graded response was most dramatic in the gal2Δ strain. The tetO$_2$:GAL2 strain also demonstrated a slightly graded response to galactose with a higher mean fluorescence at all concentrations compared to the gal2Δ strain consistent with the population-averaged data (FIG. 5D). The three strains exhibited similar population distributions in the fully induced state, or at high galactose concentrations, with a majority of the population expressing the maximum level of GFP. Slight differences in the negative populations between the tetO$_2$: GAL2 strain and the wild-type account for the differences in maximum induction at the population-averaged level.

Deletion of the Galactokinase Results in Multiple Stable Populations

Figure 1C:
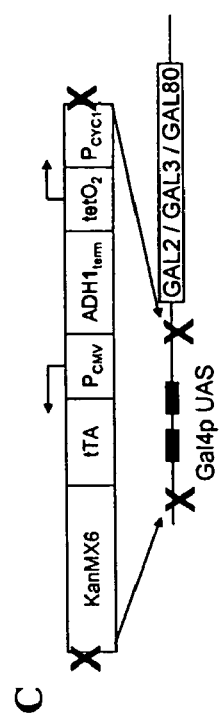
Figure 6:
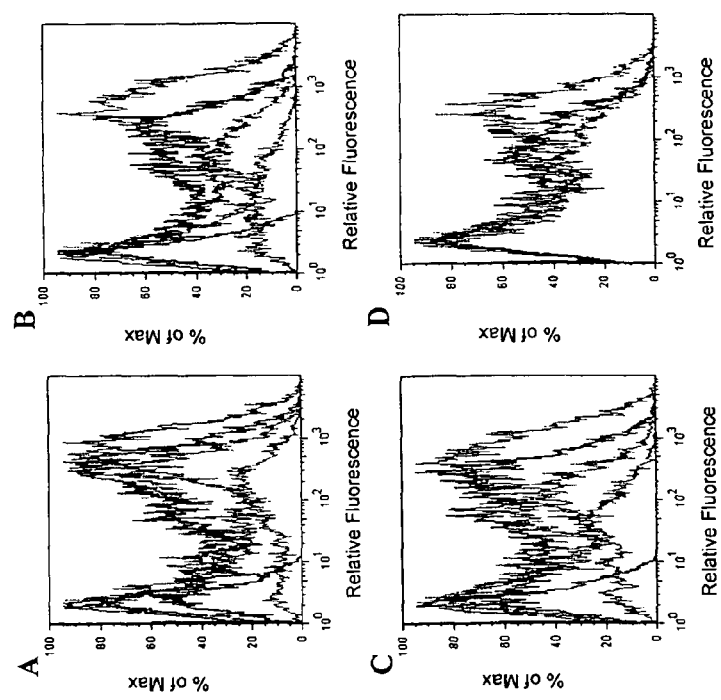
FIGS. 6A-6D are graphs showing the population response from strains with no Gal1p activity. For panels A, B, and C galactose concentration is indicated in five curves, from left to right, as 0%, 0.2%, 0.5%, 1%, and 3%. A, Population distribution of cells with the native Gal2p positive feedback control loop and no Gal1p (gal1Δ) across various concentrations of galactose. B, Population distribution of cells with constitutive Gal2p levels and no Gal1p (gal1Δ tetO$_2$:GAL2) under non-repressed conditions (0 μg/mldoxycycline) across various concentrations of galactose. C, Population distribution of cells with no Gal2p and Gal1p (gal1Δ gal2Δ) across various concentrations of galactose. D, Population distributions in 0.5% galactose from gal1Δ cells exhibiting Gal2p feedback control and no Gal1p (left most curve), gal1Δ tetO$_2$:GAL2 cells exhibiting constitutive Gal2p control and no Gal1p (middle curve), and gal1Δ gal2Δ cells exhibiting no Gal2p and Gal1p activity (right most curve).

Studies support the regimed effects of the galactokinase Gal1p on the steady-state population-averaged response of the GAL network as a result of its role in the high-affinity Gal2p transport mechanism. The effects of the removal of Gal1p in a variety of Gal2p regulatory backgrounds on the population response of the network were determined. Flow cytometry analysis was conducted to determine the population response in the absence of Gal1p. Gal1Δ, gal1Δ gal2Δ, and gal1Δ tetO$_2$:GAL2 cells were cultured under the same conditions as the population-averaged studies prior to preparation for analysis. The population data matches the general trends observed in the population-averaged data across different concentrations of galactose (FIG. 6). Interestingly, all of the Gal1p deletion strains, regardless of background, exhibited multiple, distinct cell populations across all ranges of galactose concentration measured between 0.05 and 3%. In contrast to the all-or-none response of the wild-type strain, these populations allow intermediate levels of gene expression in all gal1Δ strains Experimental Procedures Yeast Strain Construction The wild-type haploid yeast strain used in this study was W303α (MATαhis3-11, 15 trp1-1 leu2-3 ura3-1 ade2-1). All other strains were constructed by making modifications to the chromosome of this wild-type strain through standard homologous recombination procedures (FIG. 7) (*Guide to Yeast Genetics and Molecular and Cellular Biology*. (2004) Methods in Enzymology (Guthrie, C., and Fink, G., Eds.), 194. 198 vols., Elsevier Academic Press, San Francisco). For each strain an insertion cassette was constructed with the appropriate insertion sequences and regions of homology to the desired targeted sites on the chromosome. A cassette harboring an *E. coli* kanamycin resistance gene and associated promoter and terminator elements with ends homologous to regions flanking GAL2 on the chromosome was constructed by amplifying the appropriate segment from pFA6a-ZZ-TEV-S-kanMX6 (Longtine et al. (1998) *Yeast* 14, 953-961). A second cassette harboring the tetO$_2$ response element and minimal CYC1 promoter, the tTA transactivator and associated promoter and terminator elements, and the kanamycin resistance gene and associated promoter and terminator elements with ends homologous to regions flanking the GAL2 promoter was constructed in two steps (FIG. 1C). In the first step the kanamycin resistance cassette was amplified from pFA6a-ZZ-TEV-S-kanMX6 and the tetracycline-regulatable promoter cassette was amplified from pCM188 (Gari et al. (1997) *Yeast* 13, 837-848) separately. In a second round PCR step, these two cassettes were combined to form one cassette by overlap extension techniques (*Guide to Yeast Genetics and Molecular and Cellular Biology*. (2004) Methods in Enzymology (Guthrie, C., and Fink, G., Eds.), 194. 198 vols., Elsevier Academic Press, San Francisco). A third cassette harboring a *Schizosaccharomyces pombe* histidine biosynthetic gene (his5$^+$) and associated promoter and terminator elements with ends homologous to regions flanking GAL1 on the chromosome was constructed by amplifying the appropriate segment from pFA6-S-TEV-ZZ-HIS3MX6 (Longtine et al. (1998) *Yeast* 14, 953-961). Analogous cassettes with regions flanking the GAL3 and GAL80 promoters were also constructed (FIG. 1C).

The individual fragments for the GAL2, GAL3, and GAL80 promoter substitution cassettes were amplified using the TripleMaster PCR System (Eppendorf). All other cassettes were constructed with standard PCR procedures in a Dyad PCR machine (MJ Research) with Taq DNA polymerase (Roche). Oligonucleotide primers were purchased from Integrated DNA Technologies and primer sequences are available upon request. Cassettes were transformed into the appropriate strains using a standard lithium acetate procedure (Gietz et al. (2002) *Methods Enzymol.* 350, 87-96). The GAL2 knockout and GAL2, GAL3, and GAL80 tetracycline-regulatable expression cassettes were inserted into the wild-type strain. The GAL1 knockout cassette was inserted into the wild-type strain, the GAL2 knockout strain, and the GAL2 tetracycline-regulatable strain. Strains with inserted cassettes were selected by growth on synthetic complete media with the appropriate antibiotic selection and dropout media. Confirmation of cassette insertion into the correct chromosomal location was conducted by PCR amplification of the targeted region of the chromosome.

Yeast Expression Plasmids

Standard molecular biology cloning techniques were used to construct the reporter plasmid used to assay Gal4p activation (*Guide to Yeast Genetics and Molecular and Cellular Biology*. (2004) Methods in Enzymology (Guthrie, C., and Fink, G., Eds.), 194. 198 vols., Elsevier Academic Press, San Francisco). The plasmid was generated by cloning into the pCM190 (Gari et al. (1997) *Yeast* 13, 837-848) shuttle plasmid. This plasmid contains an *E. coli* origin of replication (f1) and selection marker for ampicillin resistance, as well as a *S. cerevisiae* 2 µM high copy origin of replication and a selection marker for a uracil biosynthetic gene for plasmid maintenance in synthetic complete media supplemented with the appropriate amino acid dropout solution. A yeast enhanced green fluorescent protein (yEGFP) gene with a degradation tag (CLN2-PEST) (Mateus et al. (2000) *Yeast* 16, 1313-1323) and ADH1 terminator was inserted into the multi-cloning site of pCM190 behind the tetO$_7$ promoter between BamHI and MluI restriction sites. The GAL1 promoter was then cloned into this vector between EcoRI and BamHI restriction sites. The yEGFP-CLN2-PEST gene was amplified from pSVA15 (Mateus et al. (2000) *Yeast* 16, 1313-1323) using standard PCR procedures as previously described. The GAL1 promoter was amplified from pRS314-Gal (Sikorski et al. (1989) *Genetics* 122, 19-27). This promoter contains two UASs and has been used in previous studies to measure Gal4p activity levels (Li et al. (2000) *Biotechnol. Bioeng.* 70, 187-196).

The reporter plasmid was constructed using restriction endonucleases and T4 DNA ligase from New England Biolabs. Plasmids were screened by transformation into an electrocompetent *E. coli* strain, DH10B (Invitrogen; F-mcrA Δ(mrr-hsdRMS-mcrBC) φ80dlacZΔM15 ΔlacX74 deoR recA1 endA1 araD139 Δ(ara, leu) 7697 galU galK λ-rpsL nupG), using a Gene Pulser Xcell System (BioRAD) according to manufacturer's instructions. Subcloning was confirmed by restriction analysis. Confirmed plasmids were then transformed into the appropriate S. cerevisiae strains using a standard lithium acetate protocol (Gietz et al. (2002) *Methods Enzymol.* 350, 87-96). *E. coli* cells were grown on Luria-Bertani media (DIFCO) with 100 µg/ml ampicillin (EMD Chemicals) for plasmid maintenance and S. cerevisiae cells were grown on synthetic complete media (DIFCO) supplemented with the appropriate dropout solution (Calbiochem) for plasmid maintenance. Plasmid isolation was conducted using Perfectprep Plasmid Isolation Kits (Eppendorf) according to manufacturer's instructions.

Fluorescence Assays

Cell cultures were grown at 30° C. in test tubes shaken at 200 rpm. Strains containing the reporter plasmid were grown in synthetic complete medium with the appropriate dropout media (lacking uracil) and sugar source (2% raffinose, 1% sucrose). Overnight cultures were backdiluted 30-fold into fresh noninducing-nonrepressing media to an $OD_{600}$ between 0.05 and 0.1. For assaying the network response, this fresh media contained appropriate concentrations of galactose (DIFCO), doxycycline (Sigma) for tetracycline-regulatable GAL2, GAL3, and GAL80 strains, or water (negative control). Fluorescence and $OD_{600}$ readings were measured using a Safire (TECAN) fluorescent plate reader after 8 hours. Sample volumes of 200 µL were aliquoted into 96-well flat-bottom black plates (Greiner). The excitation and emission wavelengths were set to 485 nm and 515 nm, respectively, with a bandwidth of 12 nm. Fluorescence was measured from the bottom of the plate with a gain setting of 100. Fluorescence was normalized for cell number by dividing relative fluorescence units (RFUs) by the $OD_{600}$ of the culture after subtracting the media background from each. All measurements were repeated at least in triplicate.

Flow Cytometry Assays

Yeast cells were grown according to methods detailed in fluorescence assays prior to preparation for flow cytometry analysis. After 7 hours of induction, 5 ml of cells were harvested by centrifugation at 6000 rpm for 5 min, resuspended in 5 ml of phosphate buffered saline and incubated on ice for 30 min. This wash was repeated and the cell solution was subsequently filtered through a 40 µM cell strainer (Falcon). Cells were analyzed on a FACSCalibur instrument (Becton Dickinson; San Jose, Calif.) using a 15 mW Argon laser with a 400 nm excitation wavelength and a 488 nm emission wavelength. For each sample approximately 10,000 cells were analyzed and each sample was repeated in duplicate. Data from the population fluorescence was analyzed using FlowJo software (Tree Star, Inc).

REFERENCES

1. Funk et al. (2002) *Methods Enzymol.* 350, 248-257
2. Solow et al. (2005) *Biotechnol. Prog.* 21, 617-620
3. Koller et al. (2000) *Yeast* 16, 651-656
4. Mascorro-Gallardo et al. (1996) *Gene* 172, 169-170
5. Koshland (1998) *Science* 280, 852-853
6. Verma et al. (2003) *J. Biol. Chem.* 278, 48764-48769
7. Louis et al. (2002) *Sci. STKE* 2002, PE33
8. Peng et al. (2002) *Proc. Natl. Acad. Sci. USA* 99, 8548-8553
9. Horak et al. (1997) *J. Bacteria* 179, 1541-1549
10. Lamphier et al. (1992) *Proc. Natl. Acad. Sci. USA* 89, 5922-5926
11. Nehlin et al. (1991) *EMBO 1* 10, 3373-3377
12. Ramos et al. (1989) *J. Bacteria* 171, 3539-3544
13. Schell et al. (1977) *J. Biol. Chem.* 252, 1162-1166
14. Acar et al. (2005) *Nature* 435, 228-232
15. Ruhela et al. (2004) *FEBS Lett.* 576, 119-126 16. Venkatesh et al. (1999) *Biotechnol. Prog.* 15, 51-57
17. Khlebnikov et al. (2001) *Microbiology* 147, 3241-3247
18. Morgan-Kiss et al. (2002) *Proc. Natl. Acad. Sci. USA* 99, 7373-7377
19. (2004) *Guide to Yeast Genetics and Molecular and Cellular Biology*. Methods in Enzymology (Guthrie, C., and Fink, G., Eds.), 194. 198 vols., Elsevier Academic Press, San Francisco
20. Longtine et al. (1998) *Yeast* 14, 953-961
21. Gari et al. (1997) *Yeast* 13, 837-848
22. Gietz et al. (2002) *Methods Enzymol.* 350, 87-96
23. Mateus et al. (2000) *Yeast* 16, 1313-1323
24. Sikorski et al. (1989) *Genetics* 122, 19-27
25. Li et al. (2000) *Biotechnol. Bioeng.* 70, 187-196
26. Yen et al. (2003) *Yeast* 20, 1255-1262
27. Belli et al. (1998) *Nucleic Acids Res.* 26, 942-947
28. Stagoj et al. (2005) *FEMS Microbiol. Lett.* 244, 105-110
29. Bhat, P. J., and Venkatesh, K. V. (2005) *FEBS Lett.* 579, 597-603
30. Verma et al. (2004) *Biotechnol. Appl. Biochem.* 39, 89-97
31. Wolfe et al. (1997) *Nature* 387, 708-713
32. Bhat et al. (1990) *Genetics* 125, 281-291
33. Thoden et al. (2005) *J. of Biol. Chem.* 280, 36905-36911

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A yeast cell, comprising:
   (i) a mutation in the GAL2 gene that removes positive feedback control of the expression of the GAL2 gene, wherein said mutation comprises a loss-of-function mutation in GAL2 promoter, or comprises a GAL2 deletion; and
   (ii) a nucleic acid encoding a protein of interest, an RNA, or a polypeptide that regulates the production of a compound of interest, said nucleic acid being operably linked to a GAL-responsive promoter, wherein the GAL-responsive promoter is a heterologous promoter or a promoter that is not a naturally-occurring yeast promoter,
   wherein expression of the protein of interest, the RNA, or the polypeptide has a linear response to galactose or galactose analog that binds to GAL3.

2. The yeast cell of claim 1, further comprising a mutation in the GAL1 gene.

3. The yeast cell of claim 1, further comprising a mutation in one or more genes selected from: GAL4, GAL80, and GAL3.

4. The yeast cell of claim 1, which is a *Saccharomyces cerevisiae* cell.

5. The yeast cell of claim 2, wherein mutation in the GAL1 gene results in the removal of GAL1 from the GAL network in the yeast cell.

6. The yeast cell of claim 2, wherein the GAL1 gene is operably linked to a promoter selected from: a CUP promoter, a MET promoter, a PHO promoter, a LAC promoter, a tetracycline- or tetracycline analog-responsive promoter, a $Zn^{2+}$ metallothionein promoter, a metallothionein-1 promoter, a human metallothionein IIA promoter, a mouse mammary tumor virus early promoter, a mouse mammary tumor virus LTR promoter, a triose dehydrogenase promoter, a herpes simplex virus thymidine kinase promoter, a simian virus 40 early promoter, a retroviral myeloproliferative sarcoma virus promoter, an alcohol dehygrogenase (ADH) gene promoter, a glycerol-3-phosphate (GPD) gene promoter, a TEF1 promoter, a TEF2 promoter, a YEF3 promoter, a CAM1 promoter, a TEF4 promoter, a EFB1 promoter, a CYC gene promoter, a cytomegalovirus promoter (CMV), an SV40 early promoter, a Rous Sarcoma Virus (RSV) promoter, a phosphoglycerate kinase (pGK) promoter, a chicken beta-actin promoter (CBA), a promoter capable of recognizing the T4, T3, Sp6 and T7 polymerases, a PR or PL promoter of bacteriophage lambda, a trp promoter, a recA promoter, a heat shock gene promoter, a lacZ promoter, an α-amylase promoter, a σ-specific promoter, a promoter of the bacteriophages of *Bacillus*, a *Streptomyces* promoter, an int promoter of bacteriophage lambda, a bla promoter of the β-lactamase gene of pBR322, and a chloramphenicol acetyl transferase (CAT) promoter.

7. The yeast cell of claim 1, wherein the GAL-responsive promoter is a native promoter.

8. The yeast cell of claim 1, wherein the GAL-responsive promoter is selected from: GAL1 promoter, GAL2 promoter, GAL3 promoter, GAL4 promoter, GAL80 promoter, and GAL1,10 promoter.

9. The yeast cell of claim 1, wherein the GAL-responsive promoter comprises one or more GAL4 upstream activation sequences.

10. The yeast cell of claim 1, wherein the GAL-responsive promoter is a synthetic promoter comprising one or more GAL4 upstream activation sequences.

11. The yeast cell of claim 10, wherein the synthetic promoter further comprises a constitutive promoter linked with the one or more GAL4 upstream activation sequences.

12. The yeast cell of claim 11, wherein the constitutive promoter is activated in response to galactose or the analog thereof.

13. A method for regulating the production of a protein of interest, an RNA, or a compound of interest in yeast, comprising:
(i) providing a yeast cell of claim 1; and,
(ii) contacting the cell with galactose or galactose analog that binds to GAL3 to produce a linear expression of the protein of interest, the RNA, or the compound of interest,
thereby regulating the production of the protein of interest, the RNA, or the compound of interest.

14. The method of claim 13, wherein the yeast cell further comprises a mutation in the GAL1 gene.

15. The method of claim 14, wherein mutation in the GAL1 gene results in the removal of GAL1 from the GAL network in the yeast cell.

16. The method of claim 14, wherein the GAL1 gene is operably linked to a promoter selected from: a CUP promoter, a MET promoter, a PHO promoter, a LAC promoter, a tetracycline- or tetracycline analog-responsive promoter, a $Zn^{2+}$ metallothionein promoter, a metallothionein-1 promoter, a human metallothionein IIA promoter, a mouse mammary tumor virus early promoter, a mouse mammary tumor virus LTR promoter, a triose dehydrogenase promoter, a herpes simplex virus thymidine kinase promoter, a simian virus 40 early promoter, a retroviral myeloproliferative sarcoma virus promoter, an alcohol dehygrogenase (ADH) gene promoter, a glycerol-3-phosphate (GPD) gene promoter, a TEF1 promoter, a TEF2 promoter, a YEF3 promoter, a CAM1 promoter, a TEF4 promoter, a EFB1 promoter, a CYC gene promoter, a cytomegalovirus promoter (CMV), an SV40 early promoter, a Rous Sarcoma Virus (RSV) promoter, a phosphoglycerate kinase (pGK) promoter, a chicken beta-actin promoter (CBA), a promoter capable of recognizing the T4, T3, Sp6 and T7 polymerases, a $P_R$ or $P_L$ promoter of bacteriophage lambda, a trp promoter, a recA promoter, a heat shock gene promoter, a lacZ promoter, an α-amylase promoter, a σ-specific promoter, a promoter of the bacteriophages of *Bacillus*, a *Streptomyces* promoter, an int promoter of bacteriophage lambda, a bla promoter of the β-lactamase gene of pBR322, and a chloramphenicol acetyl transferase (CAT) promoter.

17. The method of claim 13, wherein the GAL-responsive promoter responds to galactose or the analog and increases the expression of the nucleic acid.

18. The method of claim 13, wherein the yeast cell further comprises a mutation in one or more genes selected from: GAL4, GAL80, and GAL3.

19. The method of claim 13, wherein the GAL-responsive promoter is a native promoter.

20. The method of claim 13, wherein the GAL-responsive promoter is selected from: the GAL1 promoter, GAL2 promoter, GAL3 promoter, GAL4 promoter, GAL80 promoter, and GAL1,10 promoter.

21. The method of claim 13, wherein the GAL-responsive promoter comprises one or more GAL4 upstream activation sequences.

22. The method of claim 13, wherein the GAL-responsive promoter is a synthetic promoter comprising one or more GAL4 upstream activation sequences.

23. The method of claim 22, wherein the synthetic promoter further comprises a constitutive promoter linked with the one or more GAL4 upstream activation sequences.

24. The method of claim 23, wherein the constitutive promoter is activated in response to galactose or the analog.

* * * * *